(12) United States Patent
Moore et al.

(10) Patent No.: US 8,628,560 B2
(45) Date of Patent: Jan. 14, 2014

(54) ORTHOPAEDIC INSTRUMENTATION WITH INTEGRAL LOAD-BEARING MEMBERS

(75) Inventors: Kyle S. Moore, Acushnet, MA (US); James A. Oti, Franklin, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1599 days.

(21) Appl. No.: 11/715,720

(22) Filed: Mar. 8, 2007

(65) Prior Publication Data
US 2008/0221569 A1 Sep. 11, 2008

(51) Int. Cl.
*A61B 17/80* (2006.01)

(52) U.S. Cl.
USPC ............... 606/290; 606/298; 606/96; 606/88

(58) Field of Classification Search
USPC ....... 606/59, 70–71, 74, 86 R, 87–88, 92–94, 606/246–278, 280–299; 623/11.11–23.76; 16/2.1–2.5; 411/531–547
See application file for complete search history.

(56) References Cited

U.S. PATENT DOCUMENTS

| | | | | |
|---|---|---|---|---|
| 3,200,665 | A | * | 8/1965 | Wells ............................. 74/446 |
| 3,322,001 | A | * | 5/1967 | Mele ........................ 408/241 R |
| 3,495,459 | A | * | 2/1970 | McLean ..................... 74/573.12 |
| 4,603,997 | A | * | 8/1986 | Hundt et al. .................. 403/228 |
| 4,778,469 | A | * | 10/1988 | Lin et al. ...................... 128/898 |
| 5,178,621 | A | * | 1/1993 | Cook et al. ...................... 606/96 |
| 5,207,682 | A | | 5/1993 | Cripe |
| 5,403,321 | A | | 4/1995 | DiMarco |
| 5,496,371 | A | * | 3/1996 | Eppley et al. .............. 623/17.18 |
| 6,004,323 | A | * | 12/1999 | Park et al. ...................... 606/246 |
| 6,126,882 | A | * | 10/2000 | Iwinski et al. ................. 264/261 |
| 6,591,708 | B2 | * | 7/2003 | Kobayashi et al. ............. 74/446 |
| 6,656,189 | B1 | | 12/2003 | Wilson et al. |
| 6,875,113 | B2 | * | 4/2005 | Nichols .......................... 464/90 |
| 7,087,058 | B2 | | 8/2006 | Cragg |
| 7,197,959 | B2 | * | 4/2007 | Crissy ......................... 74/574.4 |
| 7,814,809 | B2 | * | 10/2010 | Shinohara ....................... 74/443 |
| 2001/0001120 | A1 | | 5/2001 | Masini |
| 2001/0037050 | A1 | | 11/2001 | Lemperle |
| 2002/0026207 | A1 | | 2/2002 | Stellon et al. |

(Continued)

FOREIGN PATENT DOCUMENTS

FR 2787699 A1 6/2000
JP 2002078712 A 3/2002

(Continued)

OTHER PUBLICATIONS

Australian Examiner's First Report in corresponding Australian Application AU2008201070, dated Apr. 24, 2012 (3 pages).

(Continued)

*Primary Examiner* — Kevin T Truong
*Assistant Examiner* — Matthew Lawson
(74) *Attorney, Agent, or Firm* — Maginot, Moore & Beck, LLP

(57) ABSTRACT

An orthopaedic instrument includes a metallic load-bearing member and a non-metallic support structure formed integrally with the load-bearing member such that the load-bearing member is permanently attached to the non-metallic support structure. The non-metallic support structure enables the orthopaedic instrument to be lighter than an all-metal instrument while the metallic load bearing member provides wearability comparable to an all-metal instrument.

4 Claims, 9 Drawing Sheets

(56) References Cited

U.S. PATENT DOCUMENTS

| | | |
|---|---|---|
| 2002/0165549 A1 | 11/2002 | Owusu-Akyaw et al. |
| 2003/0109858 A1 | 6/2003 | Koseki |
| 2004/0215195 A1* | 10/2004 | Shipp et al. ............... 606/69 |
| 2004/0225291 A1* | 11/2004 | Schwammberger et al. ... 606/71 |
| 2004/0254579 A1* | 12/2004 | Buhren et al. ............... 606/71 |
| 2005/0027226 A1 | 2/2005 | Stutz et al. |
| 2005/0033298 A1* | 2/2005 | Hawkes et al. ............... 606/61 |
| 2005/0050985 A1* | 3/2005 | Crissy ............... 74/574 |
| 2005/0165400 A1* | 7/2005 | Fernandez ............... 606/69 |
| 2005/0240196 A1 | 10/2005 | Davis et al. |
| 2006/0111725 A1 | 5/2006 | Biegun |
| 2006/0116678 A1* | 6/2006 | Impellizzeri ............... 606/69 |
| 2006/0263145 A1 | 11/2006 | Pal |

FOREIGN PATENT DOCUMENTS

| | | |
|---|---|---|
| JP | 2004321725 A | 11/2004 |
| JP | 3113089 U | 9/2005 |
| JP | 2006507877 A | 3/2006 |
| WO | 2005039651 A2 | 5/2005 |
| WO | WO2008035198 A2 | 3/2008 |

OTHER PUBLICATIONS

Japanese Office Action corresponding to Japanese Patent Application JP 2008-057624, dated Oct. 2, 2012 (4 pages).

* cited by examiner

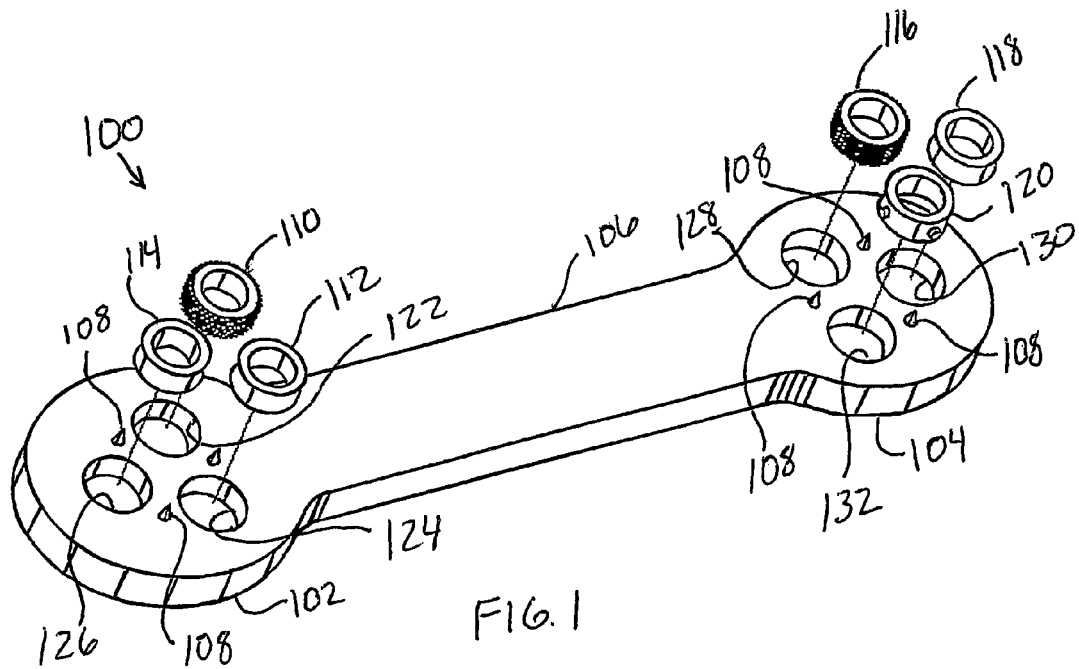
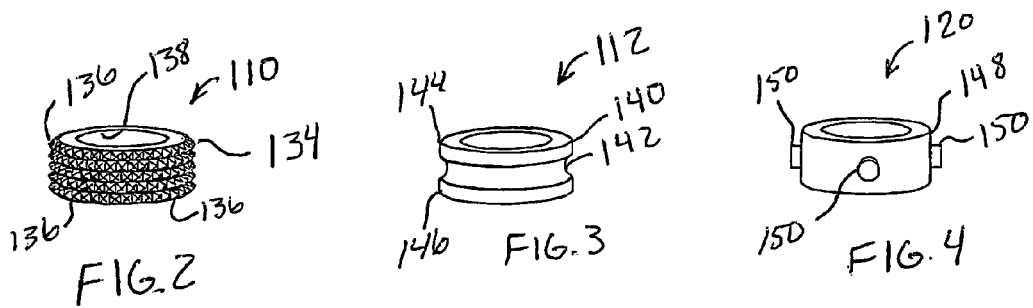
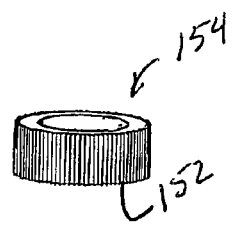

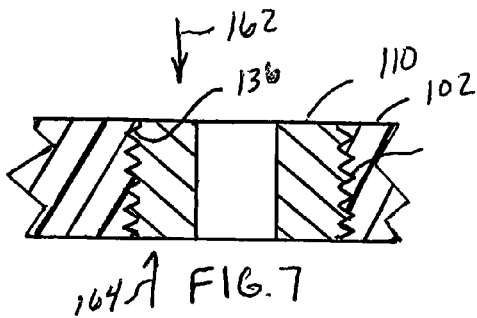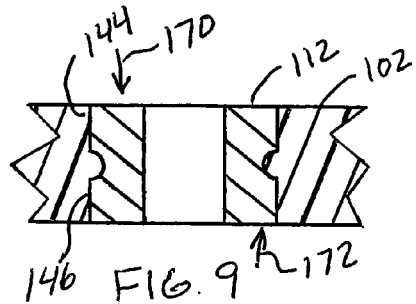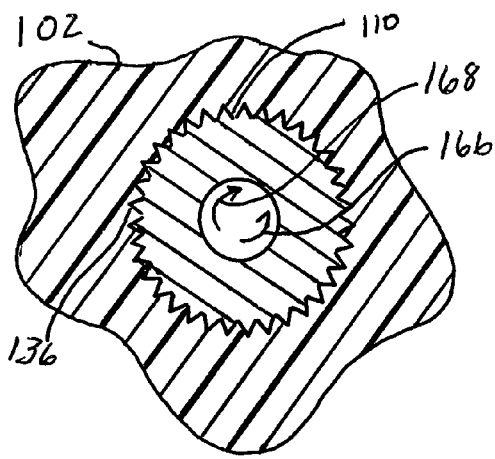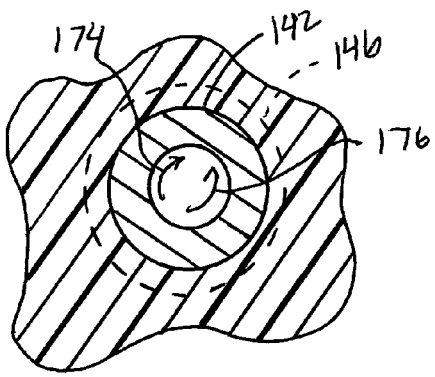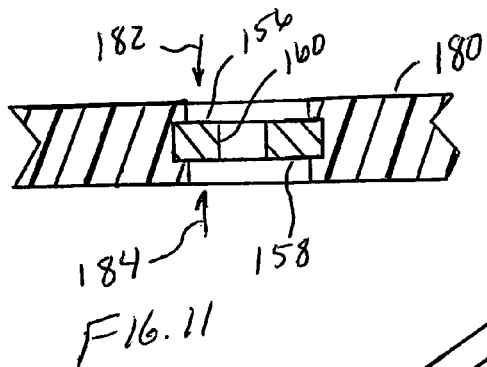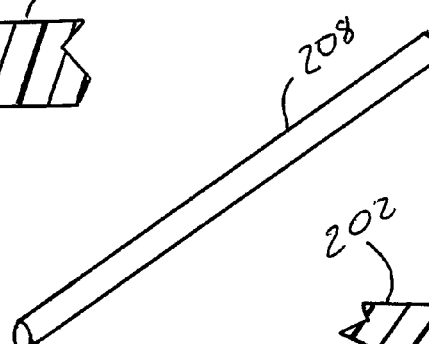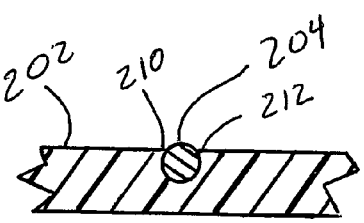

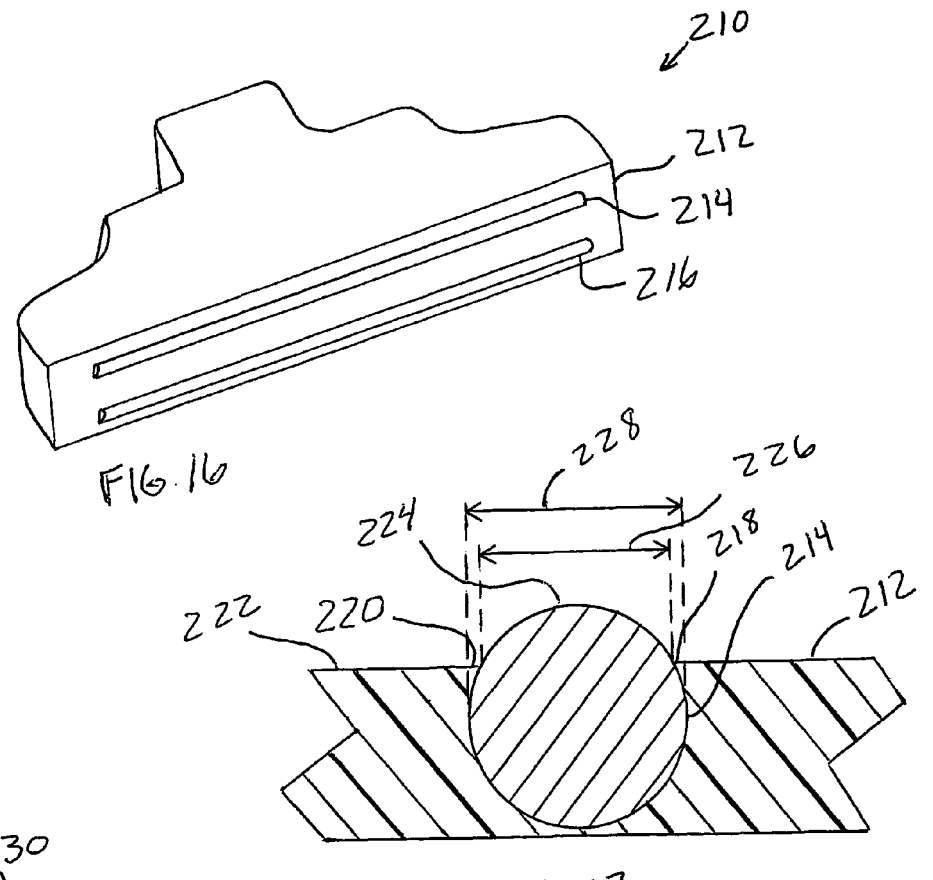
FIG. 16
FIG. 17
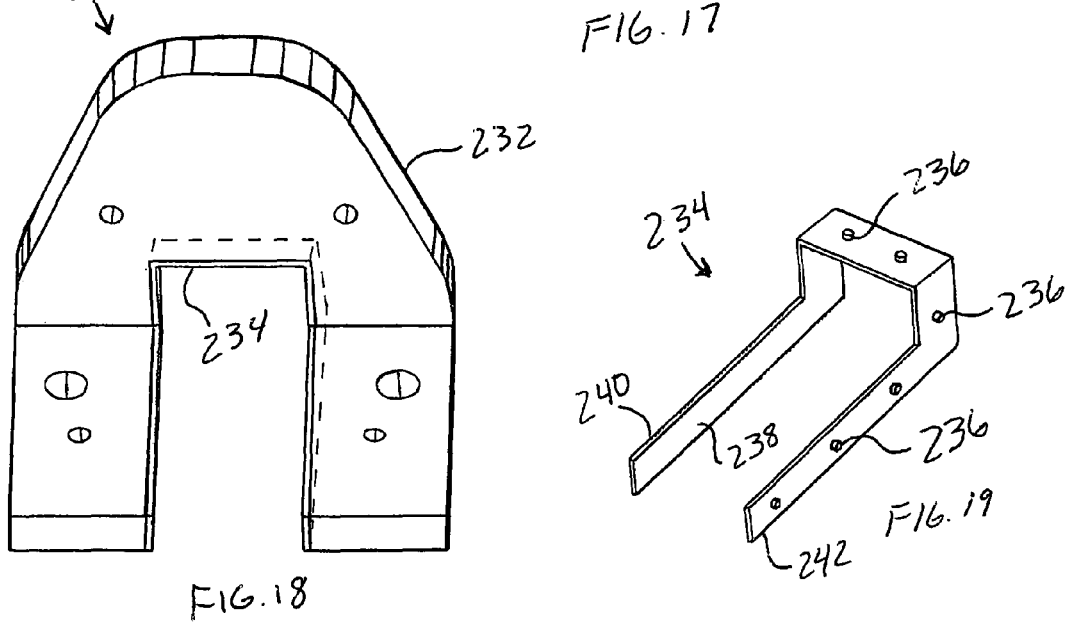
FIG. 18
FIG. 19

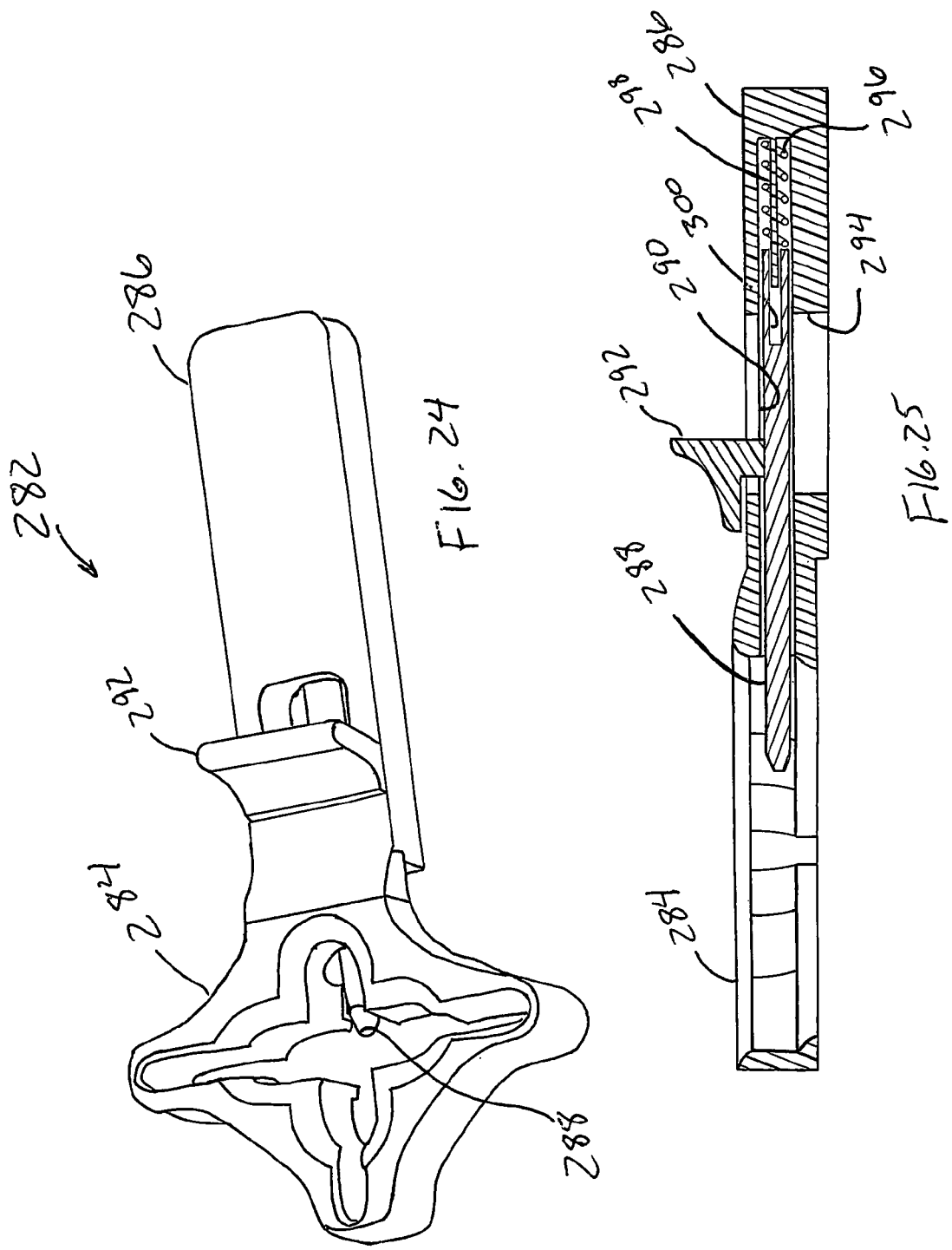

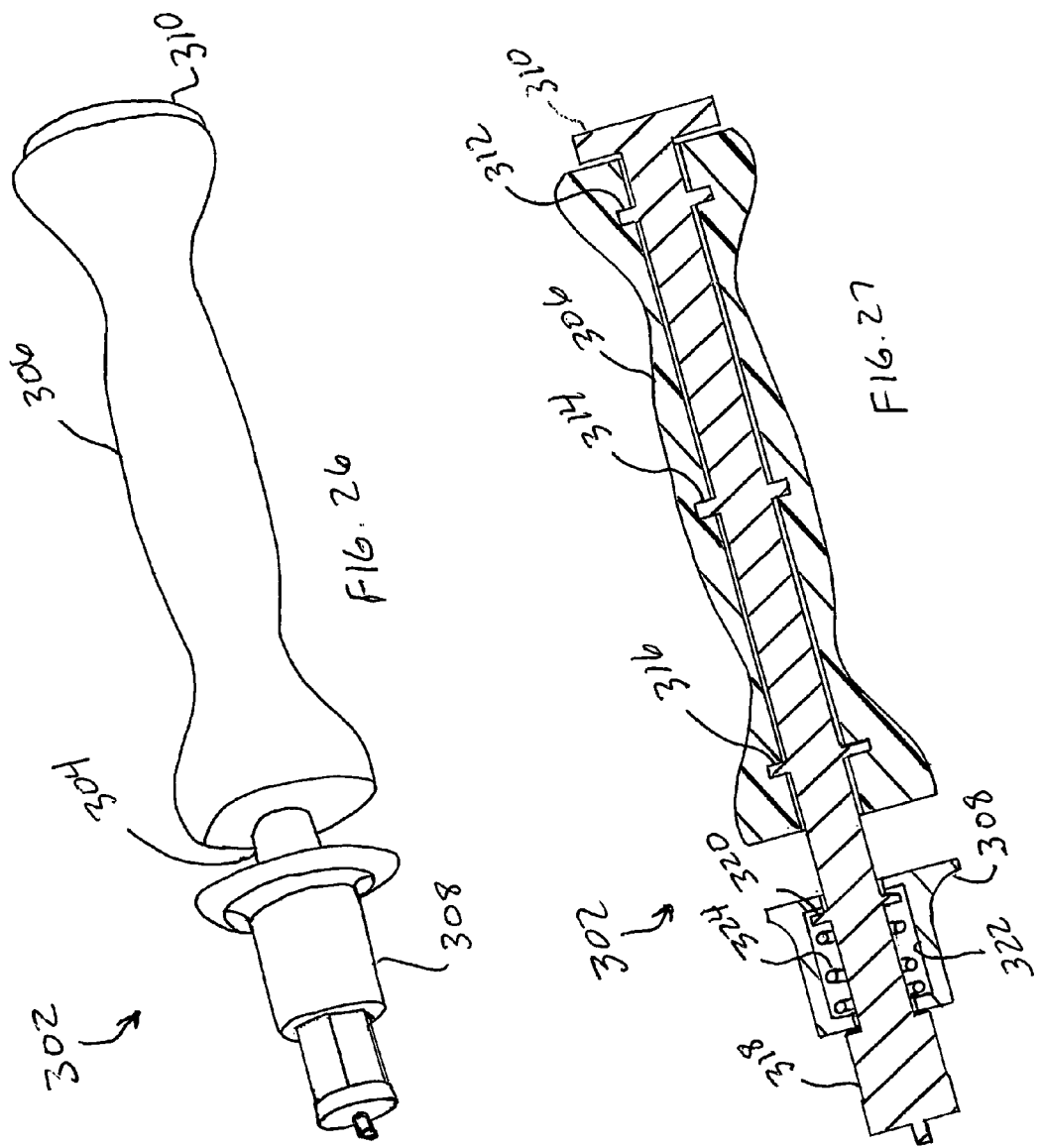

ORTHOPAEDIC INSTRUMENTATION WITH INTEGRAL LOAD-BEARING MEMBERS

FIELD OF THE INVENTION

This invention relates to the field of orthopaedics and more particularly to methods and instrumentation used in orthopaedic procedures.

BACKGROUND

Bones can become damaged as a result of accident or illness. Such damage can be, for example, to the articular cartilage covering the ends of the bones at a joint as well as the intra-articular cartilage between the ends of the adjacent bones of the joint. When the damage to the joint is severe, a joint endoprosthesis can be implanted to improve the comfort and mobility of the patient.

Joint endoprostheses have been developed to replace native tissue of several human joints. There are a variety of knee prostheses, hip prostheses, shoulder prostheses, ankle prostheses and wrist prostheses available to relieve patient suffering. Such devices are made by and available from, for example, DePuy Products, Inc. and DePuy Orthopaedics, Inc. of Warsaw, Ind.

Standard joint endoprostheses include metal components that are affixed to the articulating ends of the bones of the joint and commonly include a bearing component positioned between the metal components. Standard bearing components of joint endoprostheses have a surface against which one of the metal components articulates. For example, hip endoprostheses include a metal femoral component to be affixed to the proximal femur and a metal cup to be affixed to the acetabulum. Many of these standard hip endoprostheses include a liner in the acetabular cup against which the femoral component articulates. Knee prostheses commonly include a femoral component to be affixed to the distal femur and a tibial component to be affixed to the proximal tibia. Bearings are typically between the femoral and tibial components. Similar systems with bearings are available to replace other joints in the body. Such endoprosthesis systems are commercially available from DePuy Orthopaedics, Inc. of Warsaw, Ind.

Orthopaedic prosthetics are also used to replace bone lost in the treatment of various bone cancers. These orthopaedic prosthetics may include elements of a joint endoprosthesis as well as components to replace intercalary bone loss. Such prosthetics are made by and available from DePuy Products, Inc. and DePuy Orthopaedics, Inc. of Warsaw, Ind.

Trauma products are also available for treating patients suffering traumatic injury, such as bone fractures. Trauma products frequently include orthopaedic components such as bone screws, bone nails, bone plates and fixators, for example. Such trauma products are commercially available from DePuy Trauma and Extremities of Warsaw, Ind.

Each of the foregoing types of devices typically requires a specialized set of instruments to ensure that the devices are properly implanted. Moreover, each of the different devices may require instruments of different sizes so as to ensure proper placement of the devices for different bone sizes. Accordingly, a large number of instruments are maintained in inventory, either at the care facility or under the control of a representative of the instrument manufacturer merely to support the implantation of the orthopaedic prosthetics.

Additionally, for a single surgery, such as a hip, knee, shoulder, and other joint replacement surgery (partial or total), six or more trays of instruments and trial implants may be required to be available for potential use. Prior to use in a subsequent procedure, each tray has to be re-sterilized even if the particular tray was not utilized during a prior procedure.

Therefore, a large number of instruments, some of which may be rarely used, must still be made available. The maintenance of a large inventory, while necessary, is not advantageous for many reasons. The instruments used in surgical procedures, for example, are typically fabricated from a metal such as stainless steel using traditional manufacturing processes such as machining, turning, and drilling. Although the foregoing materials and processes result in the production of effective instruments, the instruments are very heavy and expensive. Accordingly, the required instrument inventory is both extensive and expensive. Moreover, the instruments are heavy making movement of the instruments about a care facility cumbersome.

By way of example, patella drill guide instruments are regularly used in orthopaedic procedures. Typically, these instruments are produced by machining a stainless steel block. The areas that are subjected to the highest wear or load, however, are the actual guide holes. Thus, the bulk of the stainless steel merely adds to the weight and the expense of the device. Additionally, spikes are typically desired to be provided in order to facilitate stability of the guide during use. Because patella drill guide instruments are made of stainless steel, the addition of spikes requires welding the spikes onto the stainless steel block and then polishing and finishing the weld. Thus, the manufacturing steps and associated costs of the patella guide instruments are increased.

As a further example, known femoral distal cutting block instruments require a number of precision machining operations to produce the base block and pawl. Likewise, finishing guides require machining operations to form the various plates as well as turning operations to manufacture screws needed for assembly of the finishing guide.

The problems associated with the need to maintain a large inventory of heavy instruments is further compounded by the fact that some instruments are needed merely to manipulate other instruments. One such instrument is a tibial tray trial. The tibial tray trial includes a tray instrument which is machined in several steps as well as a handle instrument. The handle instrument is designed to be attached to the tray instrument and then to be removed once the tray instrument is in the desired position. Thus, additional instruments are required. Additionally, the release mechanism used, in addition to being heavy, includes a number of additional components, thereby increasing the complexity of the instrumentation.

In addition to the foregoing limitations, any delay due to the shipping and re-sterilization of the instruments adds to the cost of providing the instruments. Also, as implant systems or instruments are modified or replaced, the inventory of such systems or instruments must also be replaced.

Therefore, a need exists for an orthopaedic instrument which is lighter than an all-metal instrument but which provides wearability comparable to the all-metal instrument. A further need exists for an instrument which is inexpensive and which is easy to manufacture. A further need exists for new complex instrumentation to be rapidly and inexpensively produced.

SUMMARY

Orthopaedic instrumentation and a method of manufacturing the instrumentation is disclosed. In one embodiment, an orthopaedic instrument includes a metallic load-bearing member and a non-metallic support structure formed integrally with the load-bearing member such that the load-bearing member is permanently attached to the non-metallic support structure.

In a further embodiment, an orthopaedic instrument includes at least one metallic work piece including a working surface and a surface interlock feature and a non-metallic support structure integrally formed with the surface interlock feature such that the at least one metallic work piece is permanently embedded in the non-metallic support structure.

In one method, manufacturing an orthopaedic instrument includes machining a metallic load-bearing member, generating a surface interlock feature on the metallic load-bearing member and forming a non-metallic support member into contact with the surface interlock feature.

DESCRIPTION OF THE DRAWINGS

FIG. 1 depicts an exploded perspective view of a patella drill guide instrument with load-bearing members which are interlocked with a support member using a variety of different surface features in accordance with principles of the present invention;

FIG. 2 depicts a perspective view of one of the load-bearing members of FIG. 1 which incorporates pyramid shaped protrusions used to form interlocks with the support member of FIG. 1 to inhibit axial and rotational movement of the load-bearing member with respect to the support member;

FIG. 3 depicts a perspective view of one of the load-bearing members of FIG. 1 which incorporates a groove to form an interlock with the support member of FIG. 1 to inhibit axial movement of the load-bearing member with respect to the support member;

FIG. 4 depicts a perspective view of one of the load-bearing members of FIG. 1 which incorporates a number of protuberances to form interlocks with the support member of FIG. 1 to inhibit rotational and axial movement of the load-bearing member with respect to the support member;

FIG. 5 depicts a perspective view of one of the load-bearing members of FIG. 1 which incorporates axially extending teeth to form interlocks with the support member of FIG. 1 to inhibits rotational movement of the load-bearing member with respect to the support member;

FIG. 6 depicts a perspective view of an alternative load-bearing member that is sized such that the upper and lower surfaces of the load-bearing member form interlocks with a support member to inhibit axial movement of the load-bearing member with respect to the support member;

FIG. 7 depicts a partial side cross-sectional view of the load-bearing member of FIG. 2 integrally formed with the support member of FIG. 1 showing the interlocks between the pyramid shaped protrusions of the load-bearing member and the support member which inhibit axial movement of the load-bearing member with respect to the support member in accordance with principles of the present invention;

FIG. 8 depicts a partial top cross-sectional view of the load-bearing member of FIG. 2 integrally formed with the support member of FIG. 1 showing the interlocks between the pyramid shaped protrusions of the load-bearing member and the support member which inhibit rotational movement of the load-bearing member with respect to the support member in accordance with principles of the present invention;

FIG. 9 depicts a partial side cross-sectional view of the load-bearing member of FIG. 3 integrally formed with the support member of FIG. 1 showing the interlocks between the groove of the load-bearing member and the support member which inhibit axial movement of the load-bearing member with respect to the support member in accordance with principles of the present invention;

FIG. 10 depicts a partial top cross-sectional view of the load-bearing member of FIG. 3 integrally formed with the support member of FIG. 1 showing the absence of interlocks between the outer periphery of the load-bearing member and the support member;

FIG. 11 depicts a partial side cross-sectional view of the load-bearing member of FIG. 6 integrally formed with a support member showing the interlocks between the upper and lower surfaces of the load-bearing member and the support member which inhibit axial movement of the load-bearing member with respect to the support member in accordance with principles of the present invention;

FIG. 14 depicts a perspective view of a rod that may be used as a load-bearing component in an instrument in accordance with principles of the present invention;

FIG. 15 depicts a partial side cross-sectional view of the load-bearing member of FIG. 14 integrally formed with a support member showing a work surface of the load-bearing member extending above the support member in accordance with principles of the present invention;

FIG. 16 depicts a perspective view of a cutting guide block instrument with a load-bearing member that is interlocked with a support member and showing a work surface of the load-bearing member extending above the support member in accordance with principles of the present invention;

FIG. 17 depicts a partial side cross-sectional view of one of the load-bearing members of FIG. 16 integrally formed with the support member wherein the interlock with the support member is formed by ledges of the support member which overhang a portion of the load-bearing member in accordance with principles of the present invention;

FIG. 18 depicts a perspective view of a finishing guide instrument with a load-bearing member that is interlocked with a support member and showing a work surface of the load-bearing member extending along various surfaces of the support member in accordance with principles of the present invention;

FIG. 19 depicts a perspective view of the load-bearing member of FIG. 18;

FIG. 24 depicts a perspective view of a keel punch guide instrument with a support member that is used to operate the load-bearing member with which it is interlocked in accordance with principles of the present invention;

FIG. 25 depicts a side cross-sectional view of the keel punch guide instrument of FIG. 24;

FIG. 26 depicts a perspective view of a universal handle instrument with a support member that is used to hold the load-bearing member with which it is interlocked in accordance with principles of the present invention;

FIG. 27 depicts a side cross-sectional view of the universal handle instrument of FIG. 26.

DETAILED DESCRIPTION

Figure 12:
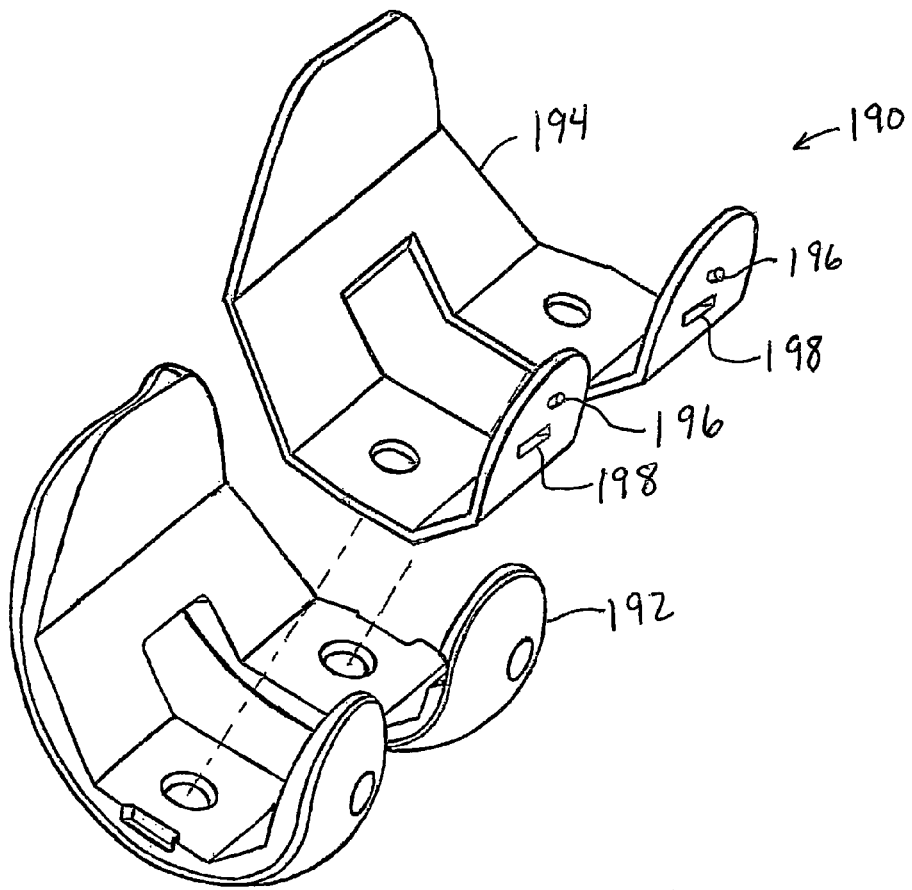
FIG. 12 depicts an exploded perspective view of a femoral trial instrument with a load-bearing member that is interlocked with a support member using protuberances and recesses in accordance with principles of the present invention.

FIG. 1 shows an exploded view of a patella drill guide 100. The patella drill guide 100 includes two guide portions 102 and 104 joined by a shaft 106. The guide portions 102 and 104 include a number of spikes 108. The guide portion 102 further includes load-bearing members 110, 112 and 114 while the guide portion 104 includes load-bearing members 116, 118 and 120. The load-bearing members 110, 112, 114, 116, 118 and 120 are located within receptors 122, 124, 126, 128, 130 and 132, respectively, which are formed in either the guide portion 102 or the guide portion 104.

The load-bearing members 110, 112, 114, 116, 118 and 120 incorporate a variety of interlocks with the guide portions 102 and 104. By way of example, the load-bearing member 110, which is shown in FIG. 2, includes an outer periphery 134 which includes a number of pyramid shaped protrusions 136. The pyramid shaped protrusions 136 provide an interlock with the guide portion 102. In contrast, the inner bore 138 of the load-bearing member 110 is smooth. This is because the inner bore 138 is a work surface since in normal use the inner bore 138 may be in contact with other instruments.

The load-bearing member 112 shown in FIG. 3 includes an outer periphery 140 that includes a groove 142 that circumscribes the load-bearing t 112. The groove 142 defines an upper flange 144 and a lower flange 146, each of these surface features is a part of an interlock. Additionally, referring to FIG. 4, the load-bearing member 120 includes an outer periphery 148 that includes a number of protuberances 150, each of which is a part of an interlock.

A load-bearing member may be provided with a variety of surface features to be used in providing an interlock in addition to those identified above. For example, the teeth 152 of the load-bearing member 154 shown in FIG. 5 and the upper surface 156 and lower surface 158 of the load-bearing member 160 may form a part of an interlock. The interlocks are used to provide a surface which acts against the surrounding support structure, such as the guide portion 102, so as to restrict movement of the load-bearing member with respect to the support structure. Thus, with reference to FIG. 7, an axial impact upon the load-bearing member 110 in the direction indicated by the arrow 162 or the arrow 164 is transferred from the pyramid shaped protrusions 136 to the guide portion 102. Likewise, rotational forces as indicated by the arrows 166 or 168 which act upon the load-bearing member 110 are transferred from the pyramid shaped protrusions 136 to the guide portion 102 as shown in FIG. 8. In both instances, the load-bearing member does not move with respect to the support member.

The forces which act upon the load-bearing members will vary depending upon the particular orthopaedic instrument. Accordingly, a surface feature may be selected for a particular load-bearing member based upon the expected forces. For example, the pyramid shaped protrusions 136 may be selected when both rotational and axial forces are encountered.

For applications wherein axial forces are the major expected force, the groove 142 may be selected. Referring to FIGS. 9 and 10, an axial impact upon the load-bearing member 112 in the direction indicated by the arrow 170 or the arrow 172 is transferred from the upper flange 144 or the lower flange 146, respectively, to the guide portion 102. Rotational forces as indicated by the arrows 174 or 176 which act upon the load-bearing member 112, however, are only transferred to the guide portion 102 through mechanisms at the juncture of the outer periphery 140 of the load-bearing member 112 and the guide portion 102 such as friction, adhesion, etc. Typically, an interlock will provide better resistance to movement than these mechanism.

Similarly, when the load-bearing member 160 is embedded within a support portion 180 of an orthopaedic instrument as shown in FIG. 11, an axial impact upon the load-bearing member 160 in the direction indicated by the arrow 182 or the arrow 184 is transferred from the upper surface 156 or the lower surface 158, respectively, to the support portion 180. Rotational forces which act upon the load-bearing member 160 are restricted by the outer periphery of the load-bearing member 160 and a portion of the upper surface 156 and the lower surface 158 through friction, adhesion, etc.

Another embodiment of an instrument is shown in FIG. 12 which shows an exploded view of a femoral trial instrument 190. The femoral trial instrument 190 includes a support member in the form of substrate 192 and a load-bearing member 194. The load-bearing member 194 includes protuberances 196 and recesses 198. The substrate 192 is formed around the protuberances 196 and within the recesses 198 to interlock the substrate and the load-bearing member 194. The load-bearing member 194 in this embodiment provides rigidity for the femoral trial 190 while the substrate 192 is formed into the more complicated contours of the articulation surfaces.

Figure 13:
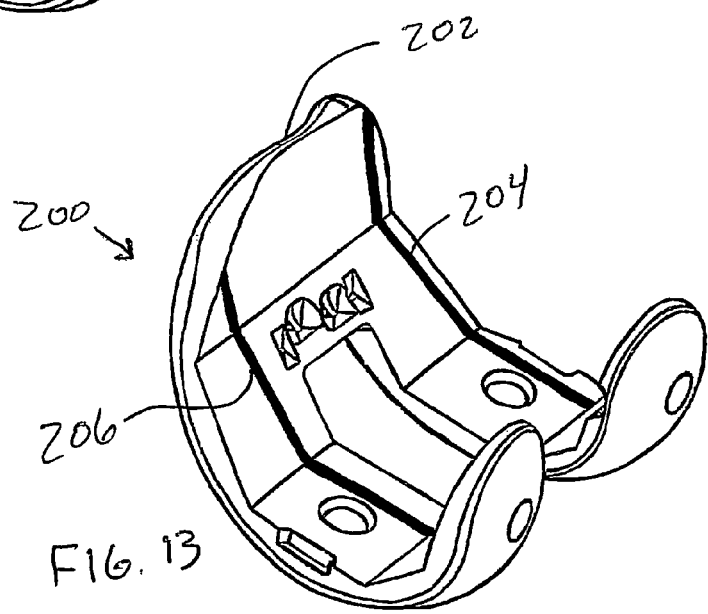
FIG. 13 depicts a perspective view of an alternative embodiment of a femoral trial instrument incorporating rods as load-bearing members in accordance with principles of the present invention.

In the embodiment of FIG. 13, a femoral trial instrument 200 includes a substrate 202 and load-bearing members 204 and 206. The substrate 202 in this embodiment is formed from a more rigid material than the substrate 192. This allows for the use of the smaller load-bearing members 204 and 206 which in this embodiment are metal rods such as the rod 208 of FIG. 14, which are bent into the desired shape.

Just like the substrate 192, the substrate 202 is formed into the more complicated contours of the articulation surfaces. In this embodiment, however, the load-bearing members 204 and 206 do not have recesses or protuberances which are used to interlock the load-bearing members 204 and 206 with the substrate 202. Rather, as shown in FIG. 15, the substrate is formed such that the lips 210 and 212 of the substrate 202 entrap the load-bearing members 204 and 206. In an alternative embodiment, the load-bearing member may be located completely within the substrate.

Partial entrapment of a load-bearing member in the manner shown in FIG. 15 may further be used to provide a work surface. The cutting guide block 210 shown in FIG. 16 includes a substrate 212 and two load-bearing members 214 and 216. The load-bearing members 214 and 216 extend above the surface of the substrate 212 to provide a work surface for contact with other instruments or devices.

With reference to FIG. 17, the load-bearing member 214 is shown with two ledges 218 and 220 at the surface 222 of the substrate 212. A work portion 224 of the load-bearing member 214 extends outwardly from the surface of the substrate 212. The ledges 218 and 220 define a chord 226 across the load-bearing member 214 which is shorter than at least one chord extending across the load-bearing member 214 and which is farther from the surface 222 of the substrate 212 than the chord 226, such as the chord 228. Accordingly, the ledges 218 and 220 interlock the load-bearing member 214 within the substrate 212 while the work surface 224 prevents other instruments or devices from contacting the substrate 212.

An alternative work surface is shown in FIG. 18 wherein a finishing guide instrument 230 includes a substrate 232 and a load-bearing member 234. As shown in FIG. 19, the load-bearing member 234 is interlocked with the substrate 232 by a number of protuberances 236. The load-bearing member 234 further includes a work surface portion 238 that extends along the entire length of the load-bearing member 234 from one arm 240 of the load-bearing member 234 to another arm 242.

Figure 20:
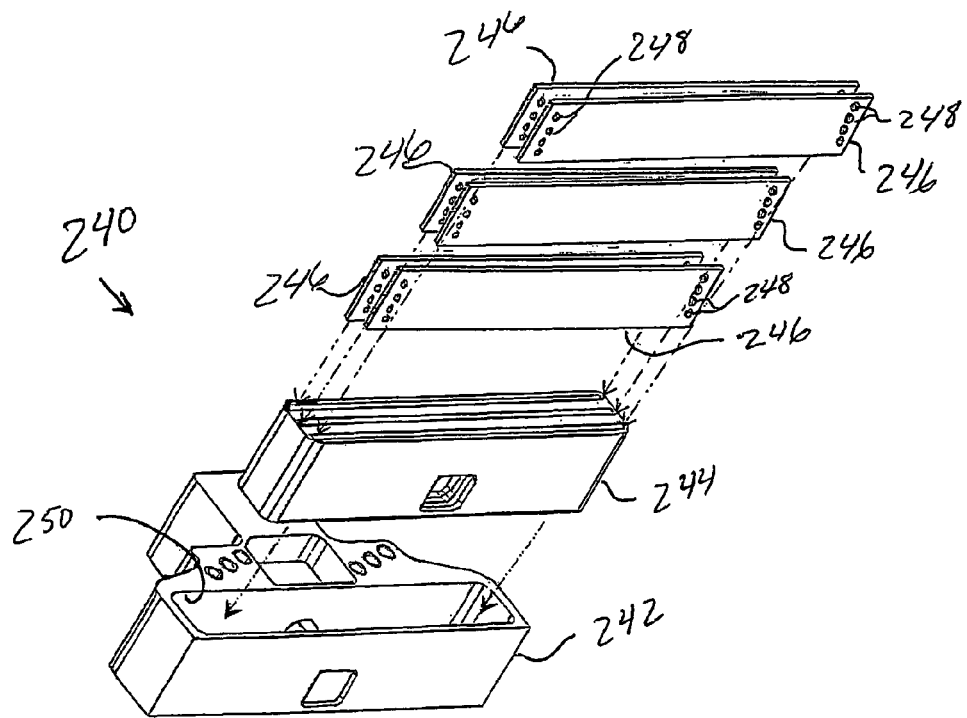
FIG. 20 depicts an exploded perspective view of a cutting block instrument with a number of load-bearing members in accordance with principles of the present invention.

FIG. 20 shows a cutting block 240 which includes a housing 242, a support substrate 244 and six load-bearing members 246. The load-bearing members 246 include a number of through holes 248. When assembled, the six load-bearing members 246 are located within the support substrate 244 which is inserted within a cavity 250 in the housing 242.

Figure 21:
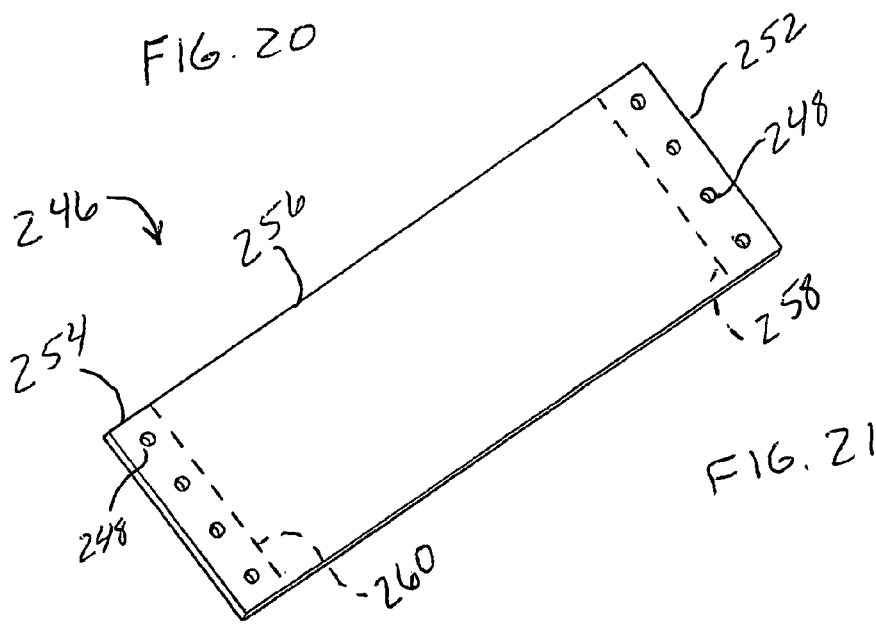
FIG. 21 depicts a perspective view of one of the load-bearing members of FIG. 20 showing a number of holes that may be over-molded with the support member to provide an interlock between the load-bearing member and the support member in accordance with principles of the present invention.

In this embodiment, the use of protuberances on the load-bearing members 246 is not desired due to the spacing restrictions within the cutting block 240. Additionally, the size of the support substrate 244 is limited by the size of the cavity 250. Accordingly the holes 248 are used as surface features which form an interlock with the support substrate 244. With reference to FIG. 21, the holes 248 are located within two end portions 252 and 254 which are separated by a work portion 256. The substrate 244 is formed about the two end portions 252 and 254. Thus, the substrate 244 extends inwardly from the end portions 252 and 254 to the dashed lines 258 and 260, respectively. The substrate 224 also extends through each of the through holes 248. Accordingly, the load-bearing member 246 is supported between two portions of the substrate 244 on either side of the end portions 252 and 254 and the two portions of the substrate are connected through the through holes 248.

Figure 22:
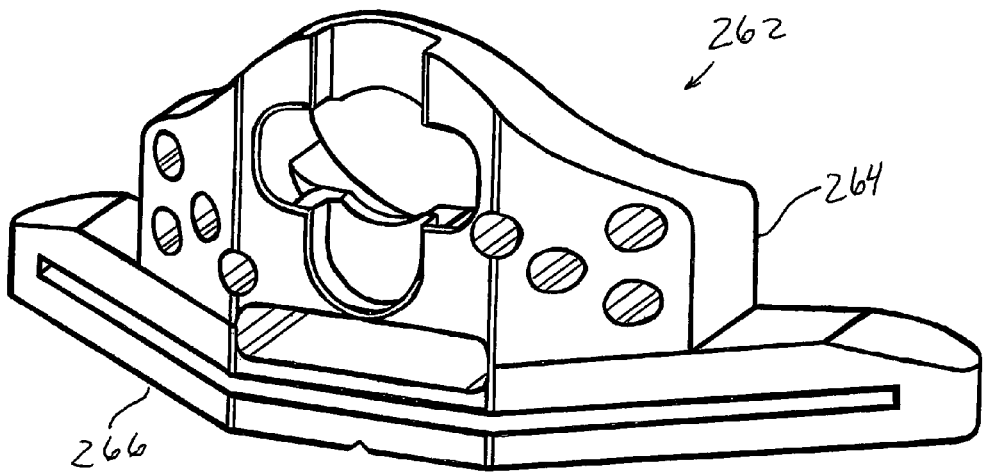
FIG. 22 depicts a perspective view of a tibial cutting block instrument with a load-bearing member in accordance with principles of the present invention.

As a matter of design choice, the load-bearing member may comprise a more substantial portion of the instrument. By way of example, FIG. 22 shows a tibial cutting block 262 which includes a body 264 and a cutting guide 266. The cutting guide 266 is made from a non-plastic material such as stainless steel while the body 264 is made from a plastic material.

In this embodiment, the load-bearing member, cutting guide 266, accounts for about one-half of the volume of the tibial cutting block 262. Of the two major components, however, the support structure, body 264, has a more complicated design. Accordingly, because the more complicated portion of the tibial cutting block 262 is molded rather than machined, the manufacture of the tibial cutting block 262 requires fewer costly manufacturing steps.

Figure 23:
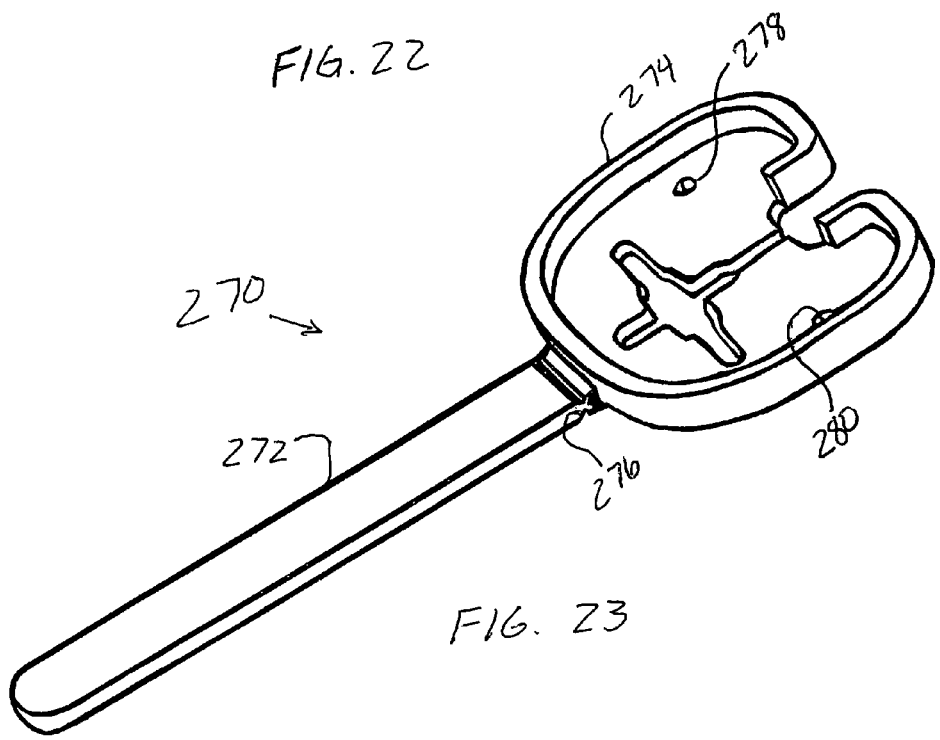
FIG. 23 depicts a perspective view of a tibial trial tray instrument with a support member that is partially removable to provide a one-time use instrument in accordance with principles of the present invention.

In a further embodiment of an instrument, a portion of the support structure is removable. FIG. 23 depicts a tibial tray trial 270 which includes a manipulating handle 272 and a tray 274. The manipulating handle 272 is connected to the tray 274 through a notch 276. Load-bearing members 278 and 280 are located in the tray 274 for use as drill guides. In this embodiment, the tray 274 and the manipulating handle 272 are made from the same non-metallic material.

The non-metallic material is selected such that the tray 274 supports the load-bearing members 278 and 280 and such that the notched area provides sufficient strength and rigidity to manipulate the tray 274 into position. The material is further selected such that the connection between the manipulating handle 272 and a tray 274 can be broken at the notch 276 when sufficient force is concentrated at the notch 276. Thus, once the tray 274 is in the desired position and fixed in place, force is applied to the manipulating handle 272 causing the manipulating handle 272 to snap at the notch 276. Accordingly, the tibial tray 270 is a single use instrument.

FIG. 24 depicts an embodiment of an instrument wherein a support member is used to operate a load-bearing member. The keel punch guide 282 includes a guide 284 and a handle 286. A pin 288 extends from an inner bore 290 of the handle 286 into the guide 284 as shown in FIG. 25. A thumb piece 292 is interlocked with the pin 288 and extends through an opening 294 in the handle 286. A spring 296 is located within the inner bore 290. The spring 296 is located about a centering pin 298 which extends into an inner bore 300 in the pin 288.

In operation, the thumb piece 292 is used to force the pin 288 against the spring 296. As the spring 296 is compressed, the pin 288 is moved further into the inner bore 290 of the handle 286 and the centering pin 298 is inserted within the inner bore 300. When the keel punch guide 282 is in the desired position, the thumb piece 292 is released and the spring 296 forces the pin 288 toward and partially into the guide 284. Accordingly, the interlock between the pin 288 and the thumb piece 292 must be sufficiently strong to allow the spring 296 to be compressed without failing.

FIG. 26 depicts a universal handle 302 that includes a load-bearing member 304, a support member 306 and an engagement mechanism 308. The load-bearing member 304 includes a metal strike plate 310 which is located outwardly of the support member 306 and three flanges 312, 314 and 316 which form interlocks with the support member 306 as shown in FIG. 27. The load-bearing member 304 further includes a coupling portion 318 and a flange 320. The flange 320 is positioned within an inner bore 322 along with a spring 324. The flange 320, the spring 324 and the engagement mechanism 308 are used to couple the universal handle 302 to other instruments.

The universal handle 302 is used to transfer impacts to an instrument or device to which the universal handle 302 is coupled. Accordingly, an operator may use a mallet to impact the metal strike plate 310 while the operator grasps the universal handle 302 about the support member 306. The load-bearing member 304 transfers the force from the impact to the coupling portion 318 which in turn transfers the impact to the coupled instrument or implant. The flanges 312, 314 and 316 are configured to ensure solid fixation of the load-bearing member 304 within the support member 306 during such impacting.

Figure 28:
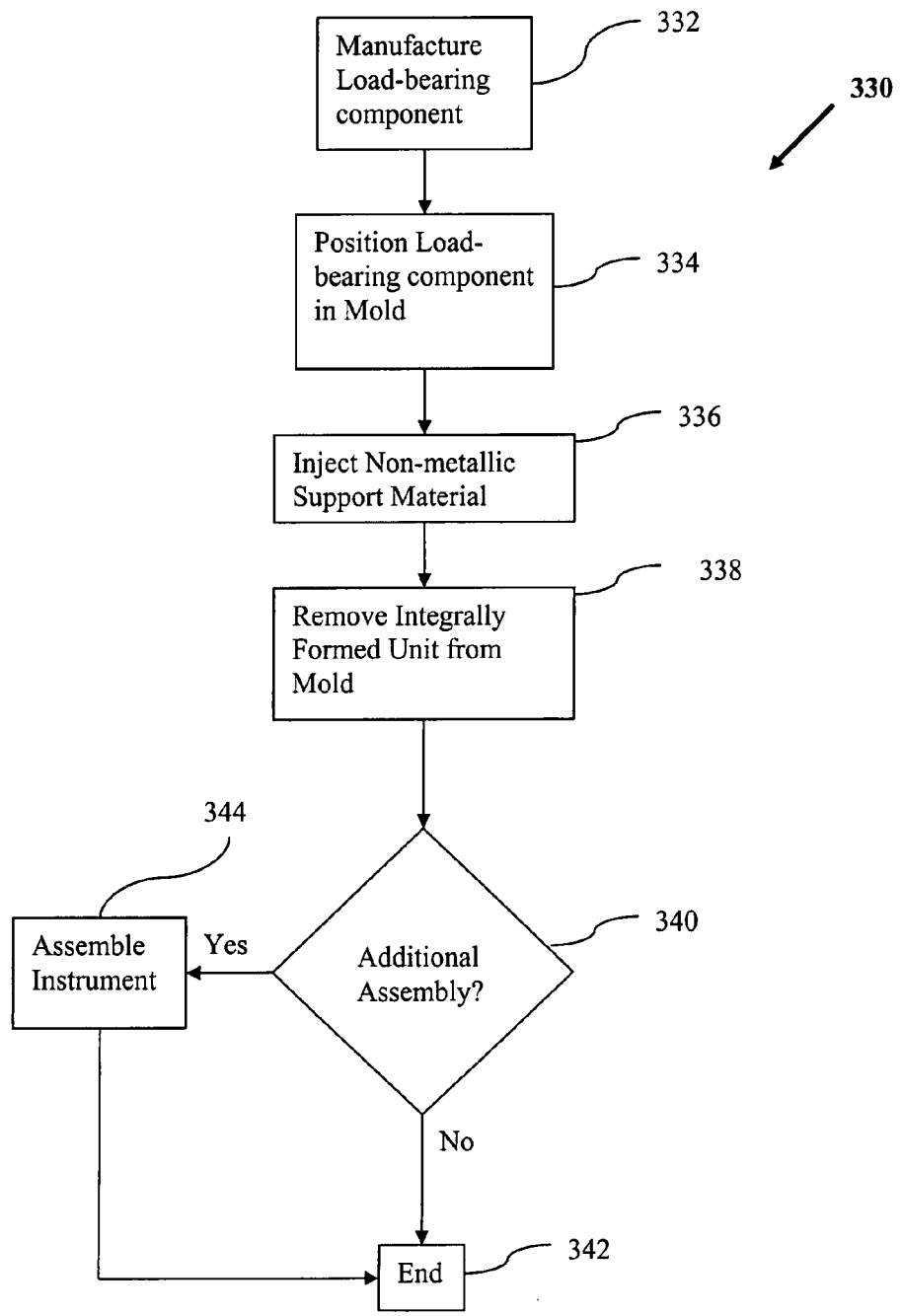
FIG. 28 depicts a process that may be used to manufacture an instrument with a load-bearing member interlocked with a support member in accordance with principles of the present invention.

In one method, the foregoing instruments are fashioned in like manner. With reference to FIG. 28, the method 330 begins at the step 332 with manufacturing the load-bearing member. The load-bearing member may be manufactured from metal materials including stainless steels, cobalt, chrome, nickel and others. The processes used in manufacturing the load-bearing member will depend upon the particular instrument as well as the type of metal. Some processes that may be used include machining, drilling, electrical discharge machining, grinding and stamping.

By way of example, the load-bearing members 110, 112, 114, 116, 118 and 120 are turned and the desired surface feature is formed thereon. The load-bearing member 194 may be machined by laser, water jet cutting, stamping or forming a blank into the desired shape and texturing the protuberances 196 and the recesses 198. The load-bearing members 204 may be cut and stamped. The load-bearing members 246 may be manufactured by cutting the desired shape out of a metal sheet and drilling the through holes 248.

Once the load-bearing member is machined, it is positioned within an injection mold at the step 334. The positioning of the load-bearing member within the injection mold may be accomplished in any acceptable manner. For example, in a different technological field, U.S. Pat. No. 6,126,882 of Iwinski et al. discloses a method of molding a socket tool with a metal insert by placing the metal insert in a mold. Once the load-bearing member is positioned, a resin is injected into the mold at the step 336. The type of resin is selected to provide the desired properties such as rigidity and strength while exhibiting reduced weight or ease of fabrication as compared to the metal used in the load-bearing member. Thus, different instruments may be produced using different resins. Acceptable resins include medical grade plastics and glass filled substrates such as polyamide polyphenylsulfone, polyethersulfone, polysulfone, polyketone and polyarylamide.

Care should be taken in the design of the injection mold to ensure adequate redundancy of interlocks and penetration of the injected resin into the surface features to form the desired interlock for he expected forces. Larger surface features such as the flanges 312, 314 and 316 in FIG. 27 may function properly as a part of an interlock even with a small cavity in the molded support member. Thus, redundant flanges may not be needed. The ability of smaller surface features such as the through holes 248 to function properly as a part of an interlock may be seriously degraded, however, by the presence of a void in the molded support member. Thus, redundant through holes and more stringent engineering of the injection mold may be needed.

Once properly cured, the integral load-bearing member and support member are removed from the injection mold at the step 338. If the instrument is substantially completed at the step 340, then the process proceeds to the step 342 and ends. By way of example, molding the support material integrally with the load-bearing material may be the final manufacturing step for the embodiments of instruments such as the patella drill guide 100, the femoral trials 190 and 200, the finishing guide instrument 230, the tibial cutting block 262 and the tibial trial tray 270.

If subsequent assembly is required at the step 330, then the instrument is assembled at the step 344 and the process ends at the step 342. Embodiments of instruments which may require assembly after a molding step include the cutting block 240, the keel punch guide 282 and the universal handle 302.

While the present invention has been illustrated by the description of exemplary processes and system components, and while the various processes and components have been described in considerable detail, the applicants do not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of the applicants' general inventive concept.

We claim:

1. An orthopaedic instrument comprising:
    a plurality of metallic load-bearing members each having an outer periphery and an inner bore; and
    a non-metallic support structure formed integrally with the load-bearing members such that the load-bearing members are permanently attached to the non-metallic support structure, the non-metallic support structure having a planar configuration with a first main surface and a second main surface;
    wherein the non-metallic support structure is formed in intimate contact with each of the outer peripheries of the metallic load-bearing members while leaving the inner bore exposed at both the first and the second main surfaces;
    wherein each of the outer peripheries of the metallic load-bearing members includes a surface feature;
    wherein the non-metallic support structure is formed of a resin material molded onto the outer periphery of each of the metallic load-bearing members in fixed contact with each surface feature to form an interlock that restricts movement of the metallic-load bearing members with respect to the non-metallic support structure; and
    wherein the non-metallic support structure includes spikes that project from the first main surface.

2. The orthopaedic instrument of claim 1, wherein the surface features comprise a plurality of pyramid shaped protrusions.

3. The orthopaedic instrument of claim 1, wherein the surface features comprise a plurality of protuberances.

4. The orthopaedic instrument of claim 1 wherein the surface features comprise flanges.

* * * * *